US012558064B2

(12) United States Patent
Tashiro

(10) Patent No.: US 12,558,064 B2
(45) Date of Patent: Feb. 24, 2026

(54) ULTRASOUND DIAGNOSTIC SYSTEM AND CONTROL METHOD OF ULTRASOUND DIAGNOSTIC SYSTEM

(71) Applicant: FUJIFILM Corporation, Tokyo (JP)

(72) Inventor: Rika Tashiro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 36 days.

(21) Appl. No.: 18/442,941

(22) Filed: Feb. 15, 2024

(65) Prior Publication Data

US 2024/0324993 A1 Oct. 3, 2024

(30) Foreign Application Priority Data

Mar. 27, 2023 (JP) ................................. 2023-050031

(51) Int. Cl.
*A61B 8/00* (2006.01)
*G01S 7/52* (2006.01)

(52) U.S. Cl.
CPC .......... *A61B 8/4472* (2013.01); *A61B 8/4427* (2013.01); *A61B 8/4488* (2013.01);
(Continued)

(58) Field of Classification Search
CPC ... A61B 8/4472; A61B 8/4427; A61B 8/4488; A61B 8/465; A61B 8/469; A61B 8/54;
(Continued)

(56) References Cited

U.S. PATENT DOCUMENTS

2003/0073894 A1* 4/2003 Chiang ..................... A61B 8/56
600/407
2013/0267851 A1* 10/2013 Takahashi .............. A61B 8/483
600/445
(Continued)

FOREIGN PATENT DOCUMENTS

JP 2012-176056 A 9/2012
JP 2018-118081 A 8/2018
(Continued)

*Primary Examiner* — Kaitlyn E Sebastian
(74) *Attorney, Agent, or Firm* — Studebaker Brackett PLLC

(57) ABSTRACT

Provided are an ultrasound diagnostic system and a control method of the ultrasound diagnostic system capable of performing advanced measurement, report creation, and the like even while improving operability and mobility of an ultrasound probe.

An ultrasound probe, a portable terminal, and a diagnostic apparatus are wirelessly connected to each other, the ultrasound probe has a probe memory, the ultrasound probe acquires echo data, including echo information before becoming an ultrasound image, through transmission and reception of an ultrasound wave with respect to a subject and stores the acquired echo data in the probe memory, the portable terminal controls the ultrasound probe and the diagnostic apparatus such that the echo data stored in the probe memory is wirelessly transmitted from the ultrasound probe to the diagnostic apparatus, and the diagnostic apparatus performs ultrasound diagnosis based on the echo data wirelessly transmitted from the ultrasound probe.

19 Claims, 8 Drawing Sheets

(52) U.S. Cl.
CPC .............. *A61B 8/465* (2013.01); *A61B 8/469*
(2013.01); *A61B 8/54* (2013.01); *A61B 8/56*
(2013.01); *G01S 7/52057* (2013.01)

(58) Field of Classification Search
CPC ......... A61B 8/56; A61B 8/565; A61B 8/5207;
G01S 7/52057; G01S 15/8915
See application file for complete search history.

(56) References Cited

U.S. PATENT DOCUMENTS

| | | | |
|---|---|---|---|
| 2017/0360415 A1* | 12/2017 | Rothberg ............. | A61B 8/4477 |
| 2019/0239855 A1* | 8/2019 | Park .................... | A61B 8/4438 |
| 2020/0323513 A1* | 10/2020 | Call .................... | G01S 7/52074 |
| 2023/0414205 A1 | 12/2023 | Murakami | |

FOREIGN PATENT DOCUMENTS

| | | | | |
|---|---|---|---|---|
| JP | 2023039624 A | * | 3/2023 | |
| WO | WO-2021029179 A1 | * | 2/2021 | ............. A61B 8/565 |
| WO | 2022201663 A1 | | 9/2022 | |

* cited by examiner

ULTRASOUND DIAGNOSTIC SYSTEM AND CONTROL METHOD OF ULTRASOUND DIAGNOSTIC SYSTEM

CROSS-REFERENCE TO RELATED APPLICATIONS

The present application claims priority under 35 U.S.C. § 119 to Japanese Patent Application No. 2023-050031, filed on Mar. 27, 2023. The above application is hereby expressly incorporated by reference, in its entirety, into the present application.

BACKGROUND OF THE INVENTION

1. Field of the Invention

The present invention relates to an ultrasound diagnostic system and a control method of an ultrasound diagnostic system for performing diagnoses on a plurality of subjects at once by using a single diagnostic apparatus.

2. Description of the Related Art

Hitherto, in the medical field, an ultrasound diagnostic apparatus using ultrasound images has been put into practical use. The ultrasound diagnostic apparatus typically comprises an ultrasound probe incorporating a transducer array, and an apparatus body connected to the ultrasound probe, and transmits an ultrasound beam from the ultrasound probe toward a subject, receives an ultrasound echo from the subject through the ultrasound probe, and electrically processes a reception signal thereof to generate an ultrasound image.

In addition, as disclosed in JP2012-176056A, JP2022-201663A, and JP2018-118081A, an ultrasound diagnostic apparatus that establishes a wireless connection between an ultrasound probe and an apparatus body has been developed to improve operability and mobility of the ultrasound probe. The data acquired by the ultrasound probe is wirelessly transmitted from the ultrasound probe to the apparatus body, and the ultrasound image is displayed on the monitor of the apparatus body.

SUMMARY OF THE INVENTION

In this way, using the ultrasound probe wirelessly connected to the apparatus body makes it possible to perform ultrasound imaging on the subject at a position away from the apparatus body, but it is necessary to view the ultrasound image displayed on the monitor of the apparatus body in order to check whether or not proper imaging has been performed, and there is a concern about compromising the mobility of the ultrasound probe.

In that respect, in recent years, a so-called handheld type ultrasound diagnostic apparatus capable of displaying the ultrasound image acquired by the ultrasound probe on a terminal side monitor of a portable terminal by controlling an operation of the ultrasound probe through the portable terminal has been devised. In the handheld type ultrasound diagnostic apparatus, it is possible to perform ultrasound imaging by using the ultrasound probe while checking the ultrasound image displayed on the terminal side monitor of the portable terminal.

However, in the portable terminal, there is a concern about being unable to sufficiently perform advanced measurement, report creation, and the like due to reasons such as limitations in specifications of hardware to be equipped, a small size in the terminal side monitor, and reduced input operability.

The present invention has been made in order to solve such a conventional problem, and an object of the present invention is to provide an ultrasound diagnostic system and a control method of the ultrasound diagnostic system capable of performing advanced measurement, report creation, and the like even while improving operability and mobility of an ultrasound probe.

According to the following configuration, the above-described object can be achieved.

[1] An ultrasound diagnostic system comprising:
an ultrasound probe;
a portable terminal; and
a diagnostic apparatus,
in which the ultrasound probe, the portable terminal, and the diagnostic apparatus are wirelessly connected to each other,
the ultrasound probe has a memory,
the ultrasound probe acquires echo data, including echo information before becoming an ultrasound image, through transmission and reception of an ultrasound wave with respect to a subject and stores the acquired echo data in the memory,
the portable terminal controls the ultrasound probe and the diagnostic apparatus such that the echo data stored in the memory is wirelessly transmitted from the ultrasound probe to the diagnostic apparatus, and
the diagnostic apparatus performs ultrasound diagnosis based on the echo data wirelessly transmitted from the ultrasound probe.

[2] The ultrasound diagnostic system according to [1],
in which the ultrasound probe has
a transducer array,
a reception unit that amplifies a reception signal output from the transducer array and converts the reception signal into a digital signal,
a beam former that phase-sums the digital signal converted by the reception unit, and
a signal processing unit that generates an ultrasound image signal based on the signal phase-summed by the beam former.

[3] The ultrasound diagnostic system according to [2],
in which the ultrasound probe wirelessly transmits the digital signal converted by the reception unit to the diagnostic apparatus as the echo data.

[4] The ultrasound diagnostic system according to [2],
in which the ultrasound probe wirelessly transmits the signal phase-summed by the beam former to the diagnostic apparatus as the echo data.

[5] The ultrasound diagnostic system according to [2],
in which the signal processing unit has
a detection section that detects the signal phase-summed by the beam former and generates a complex signal,
a log compression section that log-compresses the complex signal generated by the detection section, and
a gain processing section that performs gain processing on the signal log-compressed by the log compression section.

[6] The ultrasound diagnostic system according to [5],
in which the ultrasound probe wirelessly transmits the complex signal generated by the detection section to the diagnostic apparatus as the echo data.

[7] The ultrasound diagnostic system according to [5],
in which the ultrasound probe wirelessly transmits the
signal log-compressed by the log compression section
to the diagnostic apparatus as the echo data.

[8] The ultrasound diagnostic system according to [1],
in which the portable terminal controls the ultrasound
probe such that some pieces of the echo data designated
by a user among the echo data stored in the memory are
wirelessly transmitted to the diagnostic apparatus.

[9] The ultrasound diagnostic system according to [1],
in which the portable terminal has a terminal side monitor
and displays the ultrasound image generated based on
the echo data on the terminal side monitor.

[10] The ultrasound diagnostic system according to [9],
in which the portable terminal displays, on the terminal
side monitor, items of a plurality of processing that are
executable by the diagnostic apparatus,
a processing item selected by a user from among the
plurality of executable processing is transmitted from
the portable terminal to the diagnostic apparatus, and
the diagnostic apparatus executes processing of the item
transmitted from the portable terminal by using the
echo data wirelessly transmitted from the ultrasound
probe.

[11] The ultrasound diagnostic system according to [10],
in which a plurality of the diagnostic apparatuses wire-
lessly connected to the ultrasound probe and the por-
table terminal are provided,
the portable terminal displays, on the terminal side moni-
tor, items of a plurality of processing that are execut-
able by at least any of the plurality of diagnostic
apparatuses, and
in a case in which any of the items of the plurality of
executable processing is selected by the user, the por-
table terminal displays, on the terminal side monitor, a
diagnostic apparatus capable of executing processing
of the item selected by the user among the plurality of
diagnostic apparatuses.

[12] A control method of an ultrasound diagnostic system
including an ultrasound probe, a portable terminal, and a
diagnostic apparatus wirelessly connected to each other, the
control method comprising:
acquiring echo data, including echo information before
becoming an ultrasound image, through transmission
and reception of an ultrasound wave with respect to a
subject using the ultrasound probe;
storing the acquired echo data in a memory incorporated
into the ultrasound probe;
controlling, through the portable terminal, the ultrasound
probe and the diagnostic apparatus such that the echo
data stored in the memory is wirelessly transmitted
from the ultrasound probe to the diagnostic apparatus;
and
performing, through the diagnostic apparatus, ultrasound
diagnosis based on the echo data wirelessly transmitted
from the ultrasound probe.

In the ultrasound diagnostic system according to the
present invention, the ultrasound probe, the portable termi-
nal, and the diagnostic apparatus are wirelessly connected to
each other, the ultrasound probe acquires echo data, includ-
ing echo information before becoming an ultrasound image,
through transmission and reception of an ultrasound wave
with respect to a subject and stores the acquired echo data in
a memory, the portable terminal controls the ultrasound
probe and the diagnostic apparatus such that the echo data
stored in the memory is wirelessly transmitted from the
ultrasound probe to the diagnostic apparatus, and the diagnostic apparatus performs ultrasound diagnosis based on the
echo data wirelessly transmitted from the ultrasound probe.
Therefore, it is possible to perform advanced measurement,
report creation, and the like even while improving operabil-
ity and mobility of the ultrasound probe.

BRIEF DESCRIPTION OF THE DRAWINGS

FIG. 2 is a block diagram showing an internal configu-
ration of an ultrasound probe of the ultrasound diagnostic
system according to Embodiment 1 of the present invention.

FIG. 5 is a diagram showing a display screen of the
terminal side monitor of the portable terminal on which an
ultrasound image is displayed in Embodiment 1 of the
present invention.

FIG. 6 is a diagram showing a flow of processing of the
portable terminal, the ultrasound probe, and the diagnostic
apparatus in a case of wirelessly transmitting echo data in
Embodiment 1 of the present invention.

DESCRIPTION OF THE PREFERRED EMBODIMENTS

Hereinafter, embodiments of the present invention will be
described with reference to the accompanying drawings.

The description of configuration requirements to be
described below is made based on a representative embodi-
ment of the present invention, but the present invention is
not limited to such an embodiment.

In the present specification, a numerical range represented
by "to" means a range including numerical values described
before and after "to" as a lower limit value and an upper
limit value.

In the present specification, "same" and "identical"
include error ranges generally allowed in the technical field.

Embodiment 1

Figure 1:
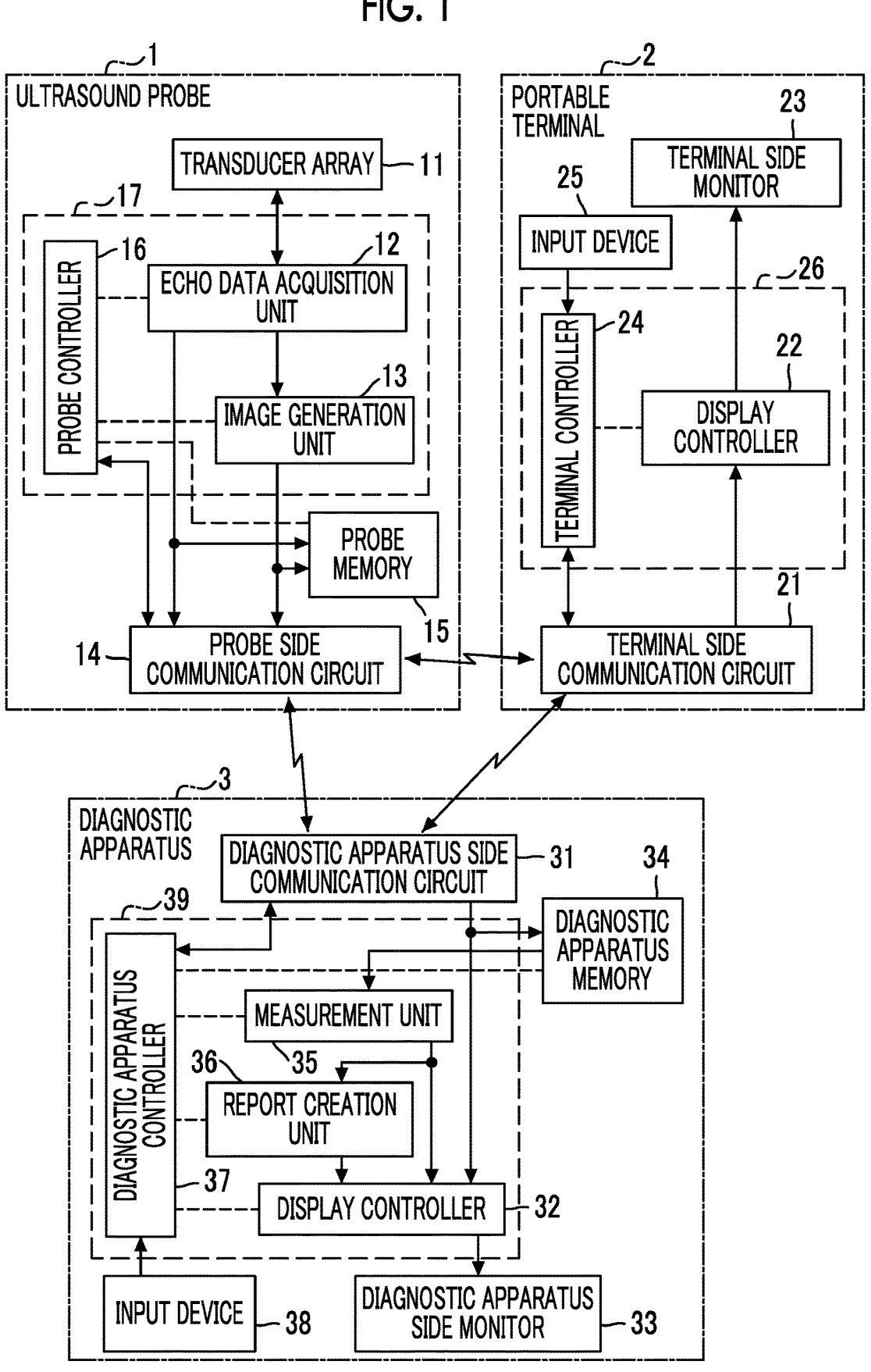
FIG. 1 is a block diagram showing a configuration of an
ultrasound diagnostic system according to Embodiment 1 of
the present invention.

FIG. 1 shows a configuration of an ultrasound diagnostic
system according to Embodiment 1 of the present invention.
The ultrasound diagnostic system comprises an ultrasound
probe 1, a portable terminal 2 wirelessly connected to the ultrasound probe 1, and a diagnostic apparatus 3 wirelessly connected to both the ultrasound probe 1 and the portable terminal 2.

The ultrasound probe 1 has a transducer array 11, and an echo data acquisition unit 12, an image generation unit 13, and a probe side communication circuit 14 are sequentially connected to the transducer array 11. In addition, a probe memory (memory) 15 is connected to each of the echo data acquisition unit 12 and the image generation unit 13, and the echo data acquisition unit 12 is also connected to the probe side communication circuit 14.

Further, a probe controller 16 is connected to the echo data acquisition unit 12, the image generation unit 13, and the probe memory 15.

A probe side processor 17 is composed of the echo data acquisition unit 12, the image generation unit 13, and the probe controller 16.

The portable terminal 2 has a terminal side communication circuit 21, and a display controller 22 and a terminal side monitor 23 are sequentially connected to the terminal side communication circuit 21. A terminal controller 24 is connected to the terminal side communication circuit 21 and the display controller 22, and an input device 25 is further connected to the terminal controller 24.

A terminal side processor 26 is composed of the display controller 22 and the terminal controller 24.

The diagnostic apparatus 3 has a diagnostic apparatus side communication circuit 31, and a display controller 32 and a diagnostic apparatus side monitor 33 are sequentially connected to the diagnostic apparatus side communication circuit 31. In addition, a diagnostic apparatus memory 34 is connected to the diagnostic apparatus side communication circuit 31, a measurement unit 35 is connected to the diagnostic apparatus memory 34, and the display controller 32 is connected to the measurement unit 35. Further, a report creation unit 36 is connected to the measurement unit 35, and the display controller 32 is connected to the report creation unit 36.

A diagnostic apparatus controller 37 is connected to the diagnostic apparatus side communication circuit 31, the display controller 32, the diagnostic apparatus memory 34, the measurement unit 35, and the report creation unit 36, and an input device 38 is further connected to the diagnostic apparatus controller 37.

A diagnostic apparatus side processor 39 is composed of the display controller 32, the measurement unit 35, the report creation unit 36, and the diagnostic apparatus controller 37.

The transducer array 11 of the ultrasound probe 1 has a plurality of ultrasound transducers that are one-dimensionally or two-dimensionally arranged. These ultrasound transducers each transmit an ultrasound wave in accordance with a drive signal supplied from the echo data acquisition unit 12, receive an ultrasound echo from a subject, and output a signal based on the ultrasound echo. For example, each ultrasound transducer includes a piezoelectric body and electrodes formed at both ends of the piezoelectric body. The piezoelectric body consists of a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), or the like.

The echo data acquisition unit 12 acquires echo data, including echo information before becoming the ultrasound image, based on a reception signal acquired by the transducer array 11 through the transmission of ultrasound waves from the transducer array 11, under the control of the probe controller 16.

Figure 2:
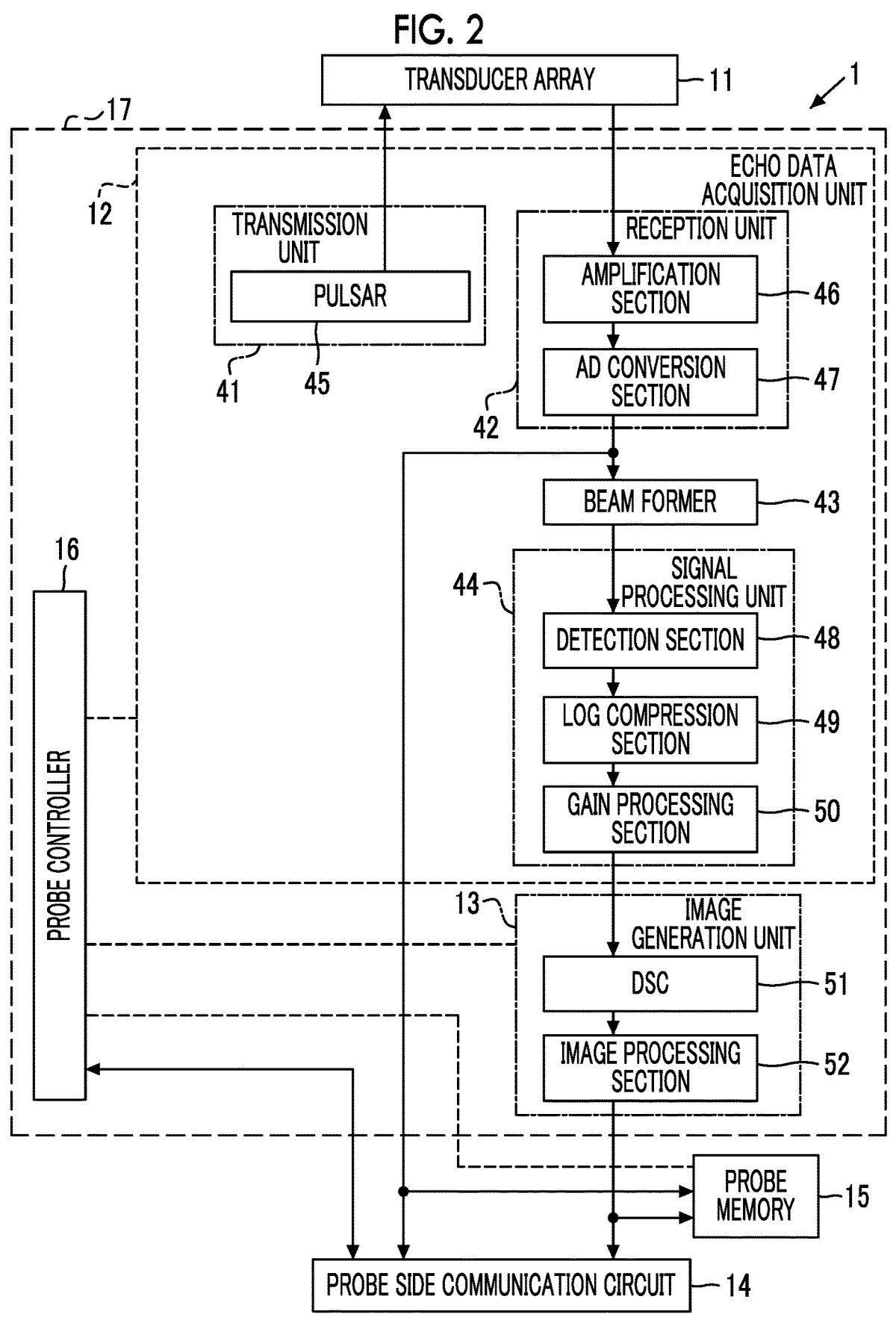

As shown in FIG. 2, the echo data acquisition unit 12 has a transmission unit 41 and a reception unit 42 that are each connected to the transducer array 11, and a beam former 43 and a signal processing unit 44 are sequentially connected to the reception unit 42. The transmission unit 41 is formed of a pulsar 45 connected to the transducer array 11. The reception unit 42 has an amplification section 46 connected to the transducer array 11 and an analog-to-digital (AD) conversion section 47 connected to the amplification section 46, and the beam former 43 is connected to the AD conversion section 47. Further, the signal processing unit 44 has a detection section 48, a log compression section 49, and a gain processing section 50 that are sequentially connected in series to the beam former 43.

The AD conversion section 47 of the reception unit 42 is also connected to the probe side communication circuit 14.

The pulsar 45 of the transmission unit 41 includes, for example, a plurality of pulse generators, and adjusts an amount of delay of each of drive signals and supplies the drive signals to the plurality of ultrasound transducers such that ultrasound waves transmitted from the plurality of ultrasound transducers of the transducer array 11 form an ultrasound beam based on a transmission delay pattern selected according to a control signal from the probe controller 16. In this way, in a case in which a pulsed or continuous wave-like voltage is applied to the electrodes of the ultrasound transducer of the transducer array 11, the piezoelectric body expands and contracts to generate a pulsed or continuous wave-like ultrasound wave from each of the ultrasound transducers, whereby an ultrasound beam is formed from the combined wave of these ultrasound waves.

The transmitted ultrasound beam is reflected in, for example, a target, such as a site of the subject, and propagates toward the transducer array 11 of the ultrasound probe 1. The ultrasound echo that propagates toward the transducer array 11 in this way is received by each of the ultrasound transducers constituting the transducer array 11. In this case, each of the ultrasound transducers constituting the transducer array 11 receives the propagating ultrasound echo to expand and contract to generate a reception signal, which is an electrical signal, and outputs these reception signals to the amplification section 46 of the reception unit 42.

The amplification section 46 amplifies the reception signal input from each of the ultrasound transducers constituting the transducer array 11 and sends out the amplified reception signal to the AD conversion section 47. The AD conversion section 47 converts the reception signal amplified by the amplification section 46 into a digital signal and sends out the converted digital signal to the beam former 43. Further, the AD conversion section 47 sends out the converted digital signal to the probe memory 15 and the probe side communication circuit 14 as echo data.

The beam former 43 performs so-called reception focus processing by applying and adding a delay to each reception data received from the AD conversion section 47. Through the reception focus processing, the sound ray signal in which each reception data converted by the AD conversion section 47 is phase-summed and a focus of the ultrasound echo is narrowed down is acquired.

The detection section 48 of the signal processing unit 44 performs quadrature detection processing and filter processing on the sound ray signal sent out from the beam former 43 to convert the sound ray signal into a complex signal, and the log compression section 49 performs compression processing using logarithmic transformation on the complex signal converted by the detection section 48.

The gain processing section 50 performs gain adjustment and dynamic range adjustment on the signal log-compressed by the log compression section 49 to generate an ultrasound image signal which is tomographic image information regarding tissues inside the subject.

In addition, as shown in FIG. 2, the image generation unit 13 has a configuration in which a digital scan converter (DSC) 51 and an image processing section 52 are sequentially connected.

The DSC 51 converts (raster-converts) the ultrasound image signal generated by the signal processing unit 44 of the echo data acquisition unit 12 into an image signal conforming to a normal television signal scanning method.

The image processing section 52 performs various types of necessary image processing, such as gradation processing, on the ultrasound image signal input from the DSC 51, and then sends out the ultrasound image signal to the probe side communication circuit 14 and the probe memory 15. Hereinafter, the ultrasound image signal that has been subjected to image processing by the image processing section 52 will be referred to as an ultrasound image.

The probe memory 15 is a memory that stores the ultrasound image generated by the image generation unit 13 and that stores the digital signal converted by the AD conversion section 47 of the reception unit 42 of the echo data acquisition unit 12 as the echo data, under the control of the probe controller 16. For example, the probe memory 15 can hold a plurality of frames of ultrasound images generated by the image generation unit 13 through ultrasound imaging on the subject, and echo data in the plurality of frames.

The echo data is stored in the probe memory 15, for example, as data in a so-called digital imaging and communications in medicine (DICOM) format having a tag in which information on the subject is stored as accessory information.

As the probe memory 15, from the viewpoint of not compromising the mobility of the ultrasound probe 1, recording media such as a flash memory, a random access memory (RAM), a solid state drive (SSD), a secure digital card (SD card), or a universal serial bus memory (USB memory) can be used.

The probe side communication circuit 14 includes an antenna for transmitting and receiving radio waves, and modulates a carrier based on the ultrasound image generated by the image generation unit 13 and the echo data acquired by the echo data acquisition unit 12, generates a transmission signal representing the ultrasound image and the echo data, and supplies the generated transmission signal to the antenna to transmit the radio waves from the antenna, thereby wirelessly transmitting the ultrasound image to the portable terminal 2 and the diagnostic apparatus 3 and wirelessly transmitting the echo data toward the diagnostic apparatus 3.

In addition, the probe side communication circuit 14 demodulates transmission signals received from the portable terminal 2 and the diagnostic apparatus 3 and sends out the demodulated transmission signals to the probe controller 16.

As the modulation method of the carrier, for example, amplitude shift keying (ASK), phase shift keying (PSK), quadrature phase shift keying (QPSK), 16 quadrature amplitude modulation (16QAM), or the like is used.

The probe controller 16 controls each unit of the ultrasound probe 1 based on a control program or the like stored in advance.

Although the probe side processor 17 having the echo data acquisition unit 12, the image generation unit 13, and the probe controller 16 is configured with a central processing unit (CPU) and a control program for causing the CPU to perform various types of processing, the probe side processor 17 may be configured with a field programmable gate array (FPGA), a digital signal processor (DSP), an application specific integrated circuit (ASIC), a graphics processing unit (GPU), or other integrated circuits (ICs) or may be configured with a combination thereof.

In addition, the echo data acquisition unit 12, the image generation unit 13, and the probe controller 16 of the probe side processor 17 can also be configured by being partially or wholly integrated into one CPU or the like.

A battery (not shown) is incorporated into the ultrasound probe 1, and power is supplied from the battery to each unit of the ultrasound probe 1.

The terminal side communication circuit 21 of the portable terminal 2 includes an antenna for transmitting and receiving radio waves, and receives the transmission signal representing the ultrasound image, which is transmitted from the probe side communication circuit 14 of the ultrasound probe 1, via the antenna and demodulates the received transmission signal, for example, through the method such as ASK, PSK, QPSK, or 16QAM, to send out the ultrasound image to the display controller 22.

Further, the terminal side communication circuit 21 modulates a carrier based on various signals generated by the terminal controller 24 to generate a transmission signal, and supplies the generated transmission signal to the antenna to transmit the radio waves from the antenna to the ultrasound probe 1 and the diagnostic apparatus 3, and further demodulates transmission signals received from the ultrasound probe 1 and the diagnostic apparatus 3 and sends out the demodulated transmission signals to the terminal controller 24.

The display controller 22 performs predetermined processing on the ultrasound image and other signals sent out from the terminal side communication circuit 21 and displays them on the terminal side monitor 23, under the control of the terminal controller 24.

The terminal side monitor 23 is used to display the ultrasound image under the control of the display controller 22, and has, for example, a display device such as a liquid crystal display (LCD) or an organic electroluminescence (EL) display.

The input device 25 is a device that is used for the user to perform an input operation, and includes, for example, a device such as a keyboard, a mouse, a track ball, a touch pad, and a touch sensor that is disposed by being overlaid on the terminal side monitor 23.

Figure 3:
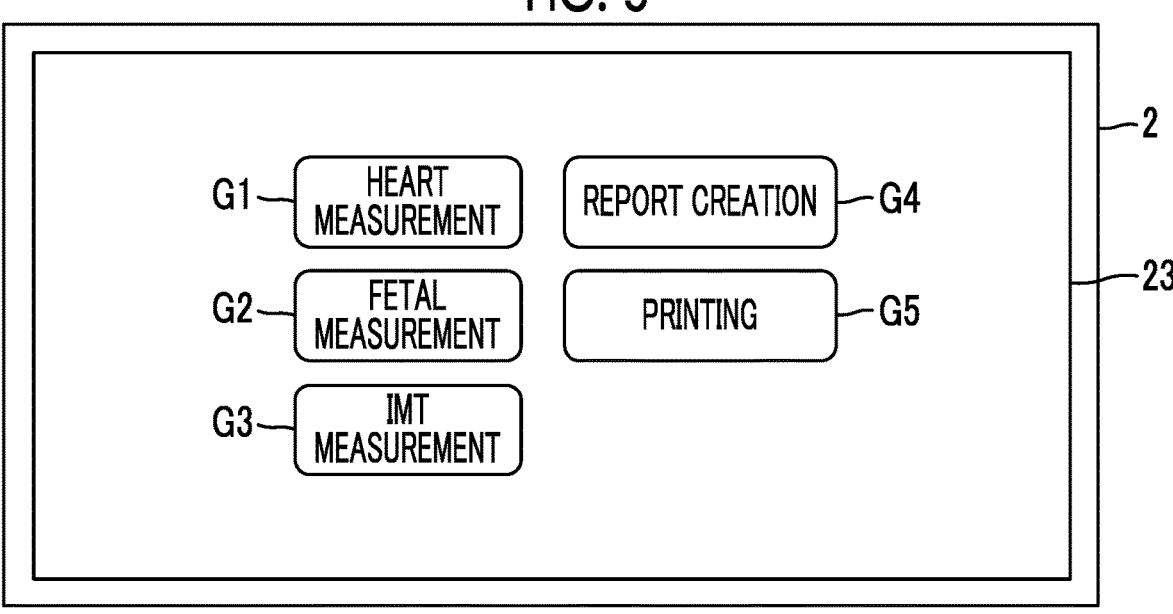
FIG. 3 is a diagram showing a display screen of a terminal
side monitor of a portable terminal on which a menu of items
of a plurality of processing executed by a diagnostic appa-
ratus is displayed in Embodiment 1 of the present invention.

The terminal controller 24 controls each unit of the portable terminal 2 based on a control program or the like stored in advance. In addition, the portable terminal 2 has a memory (not shown) in which items of a plurality of processing that are executable by the diagnostic apparatus 3 are stored in advance, and the terminal controller 24 can display a menu of the items of the plurality of processing executed by the diagnostic apparatus 3 on the terminal side monitor 23 via the display controller 22 as shown in FIG. 3. The diagnostic apparatus 3 is configured to execute processing of the selected item in response to the selection of one item by the user from the menu displayed on the terminal side monitor 23.

In the menu shown in FIG. 3, for example, an item G1 representing heart measurement, an item G2 representing fetal measurement, an item G3 representing intima media thickness (IMT) measurement, an item G4 representing report creation, and an item G5 representing printing are displayed on the terminal side monitor 23.

The terminal side processor 26 having the display controller 22 and the terminal controller 24 is configured with a CPU and a control program for causing the CPU to perform various types of processing, but the terminal side processor 26 may be configured with FPGA, DSP, ASIC, GPU, or other ICs or may be configured with a combination thereof.

In addition, the display controller 22 and the terminal controller 24 of the terminal side processor 26 can also be configured by being partially or wholly integrated into one CPU or the like.

A battery (not shown) is incorporated into the portable terminal 2, and power is supplied from the battery to each unit of the portable terminal 2.

The diagnostic apparatus side communication circuit 31 of the diagnostic apparatus 3 includes an antenna for transmitting and receiving radio waves, and receives the transmission signal representing the ultrasound image and echo data, which is transmitted from the probe side communication circuit 14 of the ultrasound probe 1, via the antenna and demodulates the received transmission signal, for example, through the method such as ASK, PSK, QPSK, or 16QAM, to send out the ultrasound image to the display controller 32 and to send out the echo data to the measurement unit 35.

Further, the diagnostic apparatus side communication circuit 31 modulates a carrier based on various signals generated by the diagnostic apparatus controller 37 to generate a transmission signal, and supplies the generated transmission signal to the antenna to transmit the radio waves from the antenna to the ultrasound probe 1 and the portable terminal 2, and further demodulates transmission signals received from the ultrasound probe 1 and the portable terminal 2 and sends out the demodulated transmission signals to the diagnostic apparatus controller 37.

The display controller 32 performs predetermined processing on the ultrasound image sent out from the diagnostic apparatus side communication circuit 31 and displays the ultrasound image on the diagnostic apparatus side monitor 33, under the control of the diagnostic apparatus controller 37.

The diagnostic apparatus side monitor 33 has, for example, a display device such as an LCD or an organic EL display, and displays the ultrasound image under the control of the display controller 32.

The diagnostic apparatus memory 34 is a memory that stores the ultrasound image and the echo data received by the diagnostic apparatus side communication circuit 31 under the control of the diagnostic apparatus controller 37.

As the diagnostic apparatus memory 34, recording media such as a flash memory, a RAM, an SSD, an SD card, a USB memory, a hard disc drive (HDD), a flexible disc (FD), a magneto-optical disc (MO disc), a magnetic tape (MT), a compact disc (CD), and a digital versatile disc (DVD) can be used.

The measurement unit 35 performs various types of measurements in accordance with an instruction input by the user via the input device 38 based on the echo data stored in the diagnostic apparatus memory 34. The echo data is obtained by amplifying the reception signal output from each of the ultrasound transducers constituting the transducer array 11 of the ultrasound probe 1 through the amplification section 46 and converting the reception signal into a digital signal through the AD conversion section 47, and is data including echo information that is before becoming the ultrasound image after gain processing.

Therefore, for example, by using phase information of each reception signal, or the like, the measurement unit 35 can execute advanced measurement that cannot be achieved only by analyzing the ultrasound image. In addition, by performing sound velocity correction based on the echo data, it is also possible to generate an ultrasound image with an improved image quality. Further, it is possible to optimize the ultrasound image itself as a target for measurement or image analysis based on the echo data, and for example, after generating the ultrasound image in one mode such as a B-mode image, it is possible to generate an ultrasound image of another mode using the echo data.

The measurement unit 35 can also perform a measurement based on the ultrasound image stored in the diagnostic apparatus memory 34.

The measurement result obtained by the measurement unit 35 is sent out to the report creation unit 36 and is displayed on the diagnostic apparatus side monitor 33 via the display controller 32.

The report creation unit 36 creates a diagnostic report based on the measurement result obtained by the measurement unit 35.

The diagnostic apparatus controller 37 controls each unit of the diagnostic apparatus 3 based on a control program or the like stored in advance.

The input device 38 is a device that is used for the user to perform an input operation, and includes, for example, a device such as a keyboard, a mouse, a track ball, a touch pad, and a touch sensor that is disposed by being overlaid on the diagnostic apparatus side monitor 33.

The diagnostic apparatus side processor 39 having the display controller 32, the measurement unit 35, the report creation unit 36, and the diagnostic apparatus controller 37 is configured with a CPU and a control program for causing the CPU to perform various types of processing, but the diagnostic apparatus side processor 39 may be configured with FPGA, DSP, ASIC, GPU, or other ICs or may be configured with a combination thereof.

In addition, the display controller 32, the measurement unit 35, the report creation unit 36, and the diagnostic apparatus controller 37 of the diagnostic apparatus side processor 39 can also be configured by being partially or wholly integrated into one CPU or the like.

Figure 4:
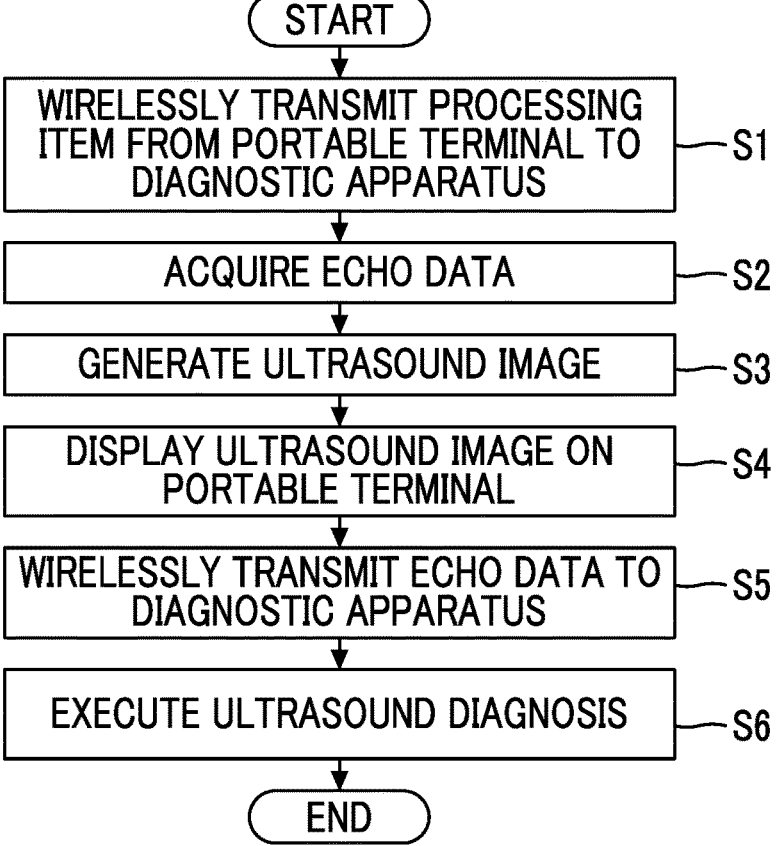
FIG. 4 is a flowchart showing an operation of the ultra-
sound diagnostic system according to Embodiment 1 of the
present invention.

Next, an operation of the ultrasound diagnostic system according to Embodiment 1 will be described with reference to a flowchart shown in FIG. 4.

First, in step S1, as shown in FIG. 3, a menu of items of a plurality of processing is displayed on the terminal side monitor 23 of the portable terminal 2, and in a case in which one item is selected by the user, the selected processing item is wirelessly transmitted from the terminal side communication circuit 21 of the portable terminal 2 to the diagnostic apparatus 3.

Next, in step S2, the ultrasound probe 1 is brought into contact with a body surface of the subject to perform ultrasound imaging, and echo data is acquired. In this case, under the control of the probe controller 16, the transmission of ultrasound waves is started from the plurality of transducers of the transducer array 11 in accordance with the drive signal from the pulsar 45 of the transmission unit 41, the ultrasound echoes from the internal tissues of the subject are received by the plurality of transducers of the transducer array 11, and a reception signal which is an analog signal is output to the amplification section 46 of the reception unit 42 and amplified and is converted into a digital signal by the AD conversion section 47.

The digital signal converted by the AD conversion section 47 is sent out from the AD conversion section 47 to the probe memory 15 as the echo data including the echo information that is before becoming the ultrasound image, and is stored in the probe memory 15.

In addition, the digital signals converted by the AD conversion section 47 are sequentially sent to the beam former 43 and the signal processing unit 44, thereby acquiring the ultrasound image signal.

In this case, the reception focus processing is performed by the beam former 43 on the digital signal converted by the AD conversion section 47, and the sound ray signal is generated. Further, the sound ray signal is subjected to quadrature detection processing and filter processing by the detection section 48 of the signal processing unit 44 and is converted into a complex signal, and the log compression section 49 performs compression processing using logarithmic transformation on the complex signal, and then the gain processing section 50 performs gain adjustment and dynamic range adjustment. In this manner, the ultrasound image signal, which is the tomographic image information regarding the tissues inside the subject, is acquired.

In subsequent step S3, the ultrasound image is generated by the image generation unit 13. That is, the ultrasound image signal generated by the signal processing unit 44 is converted into an image signal conforming to a normal television signal scanning method by the DSC 51, and is further subjected to various types of necessary image processing, such as gradation processing, by the image processing section 52, thereby becoming the ultrasound image.

Figures 5, 6:
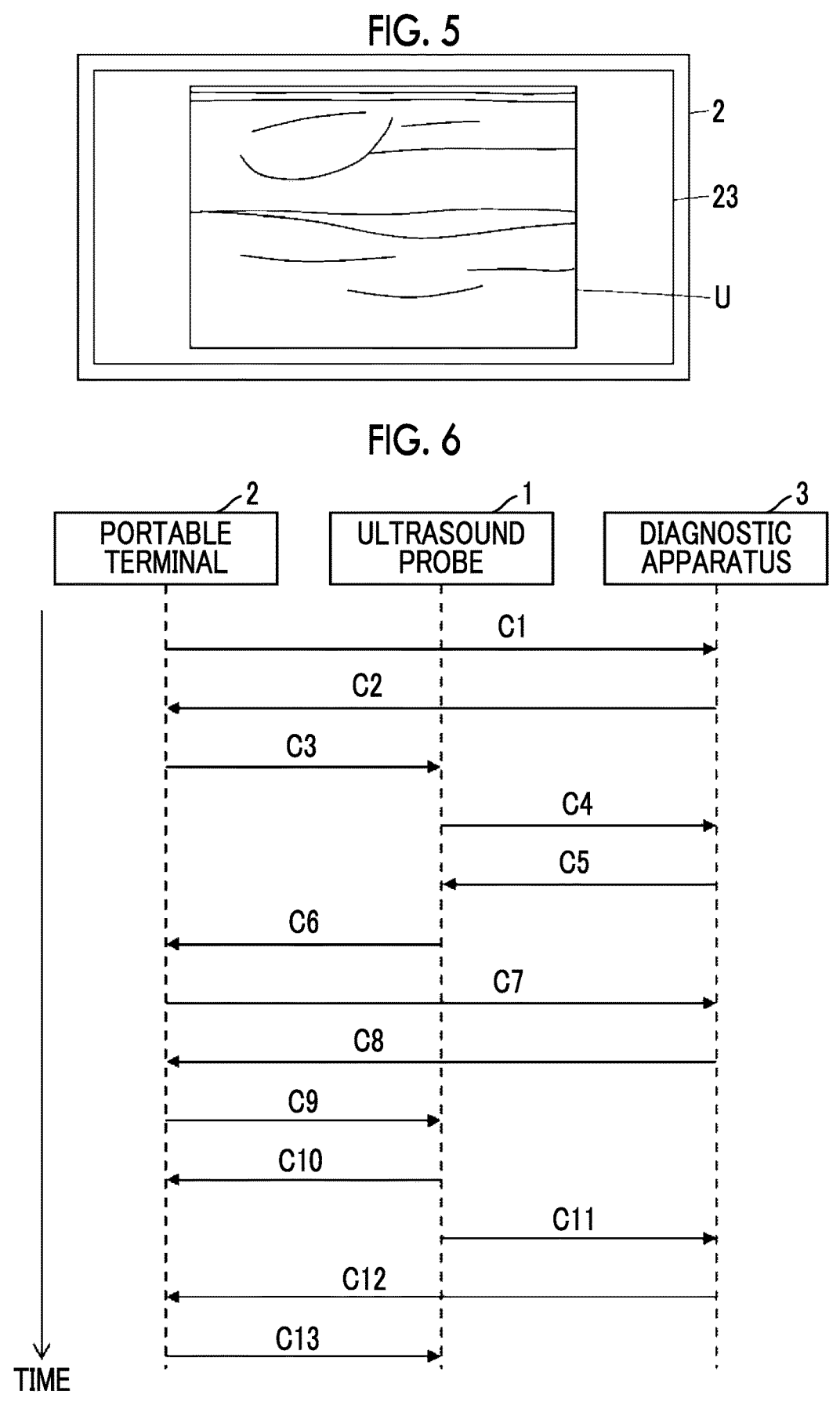

The ultrasound image generated in this manner is wirelessly transmitted from the probe side communication circuit 14 toward the portable terminal 2 under the control of the probe controller 16. Then, in step S4, as shown in FIG. 5, the ultrasound image U received by the terminal side communication circuit 21 of the portable terminal 2 is displayed on the terminal side monitor 23 via the display controller 22.

As a result, the user can perform ultrasound imaging by performing scanning with the ultrasound probe 1 while observing the ultrasound image U displayed on the terminal side monitor 23.

The echo data stored in the probe memory 15 of the ultrasound probe 1 with such ultrasound imaging, that is, the digital signal converted by the AD conversion section 47, is wirelessly transmitted from the probe side communication circuit 14 toward the diagnostic apparatus 3 in step S5.

In this case, the ultrasound probe 1 and the diagnostic apparatus 3 are controlled by the portable terminal 2, and wireless transmission of the echo data from the ultrasound probe 1 to the diagnostic apparatus 3 is performed. FIG. 6 shows a flow of processing in the portable terminal 2, the ultrasound probe 1, and the diagnostic apparatus 3.

First, a command C1 to check an activation state, a usage status, an examination function, a remaining memory capacity, and the like of the diagnostic apparatus 3 is transmitted from the portable terminal 2 to the diagnostic apparatus 3. In a case in which a command C2 to respond to the command C1 is returned from the diagnostic apparatus 3 to the portable terminal 2, the portable terminal 2 transmits a command C3 to perform the pairing-setting with the diagnostic apparatus 3 to the ultrasound probe 1, and a command C4 for a pairing request is transmitted from the ultrasound probe 1 to the diagnostic apparatus 3. In a case in which the command C5 for a pairing response is received from the diagnostic apparatus 3, the ultrasound probe 1 transmits a command C6 to issue a notification of pairing completion to the portable terminal 2.

The portable terminal 2 that has checked the pairing completion between the ultrasound probe 1 and the diagnostic apparatus 3 through the command C6 transmits a command C7 to convey a transmission mode and a transmission time of the echo data from the ultrasound probe 1 to the diagnostic apparatus 3, and in a case in which a command C8 for checking is received from the diagnostic apparatus 3, the portable terminal 2 transmits, to the ultrasound probe 1, a command C9 to designate the transmission mode and the transmission time and to issue a command for transmission start.

Examples of the transmission mode designated by the commands C7 and C9 include a mode in which all pieces of the echo data stored in the probe memory 15 are wirelessly transmitted, or a mode in which some pieces of the echo data designated by the user among the echo data stored in the probe memory 15 are wirelessly transmitted. Examples of some pieces of echo data designated by the user include echo data for the examination unit of the subject, and echo data for the ultrasound image unit, and the like. In addition, there is also a mode in which some pieces of echo data are wirelessly transmitted by designating the transmission time such that the wireless transmission is performed only for a time designated by the user.

The ultrasound probe 1 that has received the command C9 transmits a command C10 for checking to the portable terminal 2, and then wirelessly transmits the echo data stored in the probe memory 15 toward the diagnostic apparatus 3 together with a command C11 based on the transmission mode and the transmission time designated by the command C9. In a case in which the wireless transmission of the echo data is completed, a command C12 to issue information that the echo data has been received is transmitted from the diagnostic apparatus 3 to the portable terminal 2.

Finally, a command C13 is transmitted from the portable terminal 2 that has received the command C12 to the ultrasound probe 1, and in the ultrasound probe 1, the echo data wirelessly transmitted to the diagnostic apparatus 3 is erased from the probe memory 15 based on the command C13.

The echo data wirelessly transmitted from the ultrasound probe 1 to the diagnostic apparatus 3 in this manner is received by the diagnostic apparatus side communication circuit 31 of the diagnostic apparatus 3 and is stored in the diagnostic apparatus memory 34. Then, the measurement is performed by the measurement unit 35 using the echo data stored in the diagnostic apparatus memory 34 in accordance with the processing item wirelessly transmitted from the portable terminal 2 in step S1, and the ultrasound diagnosis is executed in step S6.

Here, the echo data is obtained by amplifying the reception signal output from each of the ultrasound transducers constituting the transducer array 11 of the ultrasound probe 1 through the amplification section 46 and converting the reception signal into a digital signal through the AD conversion section 47, and is data including echo information that is before becoming the ultrasound image after gain processing. Therefore, in step S1, for example, in a case in which the item G1 representing the heart measurement is selected by the user, the measurement unit 35 can use the echo data to execute advanced measurement related to heart measurement, which cannot be achieved only by analyzing the ultrasound image.

In addition, in a case in which the item G2 representing fetal measurement is selected in step S1, the measurement unit 35 executes fetal measurement using the echo data, and in a case in which the item G3 representing IMT measurement is selected in step S1, the measurement unit 35 executes the IMT measurement by using the echo data.

The measurement result obtained by the measurement unit 35 is displayed on the diagnostic apparatus side monitor 33 via the display controller 32.

Further, not only the echo data but also the ultrasound image generated by the image processing section 52 of the ultrasound probe 1 can be wirelessly transmitted from the ultrasound probe 1 to the diagnostic apparatus 3 and stored in the diagnostic apparatus memory 34. Therefore, the ultrasound image can be displayed on the diagnostic apparatus side monitor 33 of the diagnostic apparatus 3, and the measurement unit 35 can also perform the measurement based on the ultrasound image stored in the diagnostic apparatus memory 34.

In addition, in a case in which the item G4 representing report creation is selected by the user from the menu displayed on the terminal side monitor 23 of the portable terminal 2, the report creation unit 36 creates a diagnostic report based on the measurement result obtained by the measurement unit 35. The created diagnostic report is displayed on the diagnostic apparatus side monitor 33 via the display controller 32.

Further, in a case in which the item G5 representing printing is selected by the user from the menu displayed on the terminal side monitor 23 of the portable terminal 2, a printing instruction is transmitted from the diagnostic apparatus side communication circuit 31 to a printer (not shown) connected to the diagnostic apparatus 3, and the measurement result, diagnostic report, and the like are printed by the printer.

Embodiment 2

Figure 7:
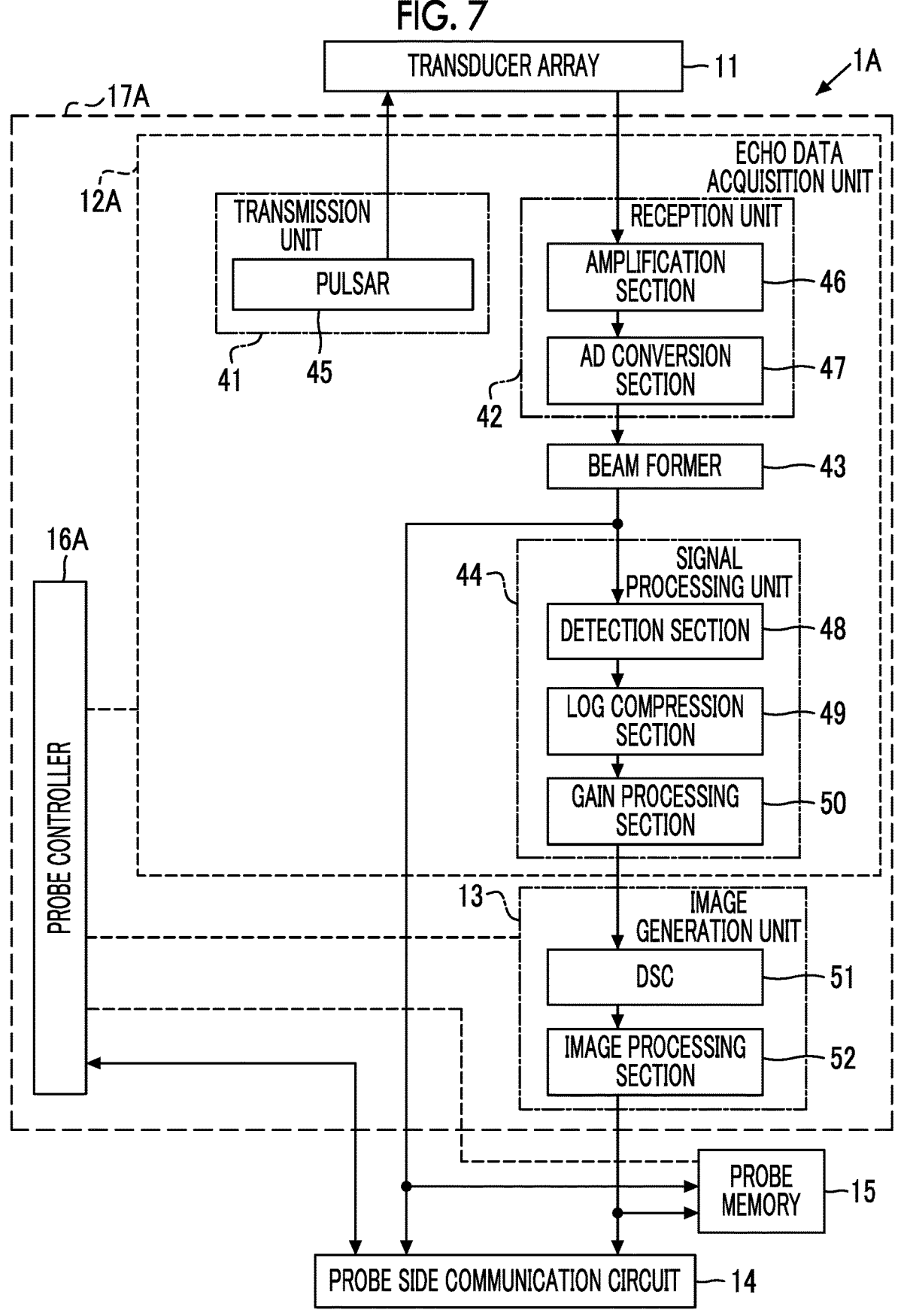
FIG. 7 is a block diagram showing an internal configu-
ration of an ultrasound probe of an ultrasound diagnostic
system according to Embodiment 2 of the present invention.

FIG. 7 shows an internal configuration of an ultrasound probe 1A of an ultrasound diagnostic system according to Embodiment 2 of the present invention. The ultrasound probe 1A uses an echo data acquisition unit 12A and a probe controller 16A instead of the echo data acquisition unit 12 and the probe controller 16 with respect to the ultrasound probe 1 in Embodiment 1 shown in FIG. 2, and other configurations are the same as those of the ultrasound probe 1 in Embodiment 1.

The echo data acquisition unit 12A has the same configuration as the echo data acquisition unit 12 of the ultrasound probe 1 in Embodiment 1. However, in the ultrasound probe 1, the AD conversion section 47 of the reception unit 42 is connected to the probe side communication circuit 14, but in the ultrasound probe 1A in Embodiment 2, the beam former 43 is connected to the probe side communication circuit 14.

The probe controller 16A is connected to the echo data acquisition unit 12A, the image generation unit 13, and the probe memory 15.

In addition, a probe side processor 17A is composed of the echo data acquisition unit 12A, the image generation unit 13, and the probe controller 16A.

The beam former 43 performs so-called reception focus processing by applying and adding a delay to each reception data received from the AD conversion section 47 to generate a sound ray signal in which each reception data converted by the AD conversion section 47 is phase-summed, but in the ultrasound probe 1A in Embodiment 2, the sound ray signal generated by the beam former 43 is sent out to the probe memory 15 and the probe side communication circuit 14 as the echo data, and is wirelessly transmitted to the diagnostic apparatus 3 under the control of the portable terminal 2.

The sound ray signal phase-summed by the beam former 43 is also data that includes echo information that is before becoming the ultrasound image after gain processing. Therefore, even in the ultrasound diagnostic system according to Embodiment 2, by using the echo data wirelessly transmitted from the ultrasound probe 1A, the measurement unit 35 of the diagnostic apparatus 3 can execute advanced measurement, which cannot be achieved only by analyzing the ultrasound image.

Embodiment 3

Figure 8:
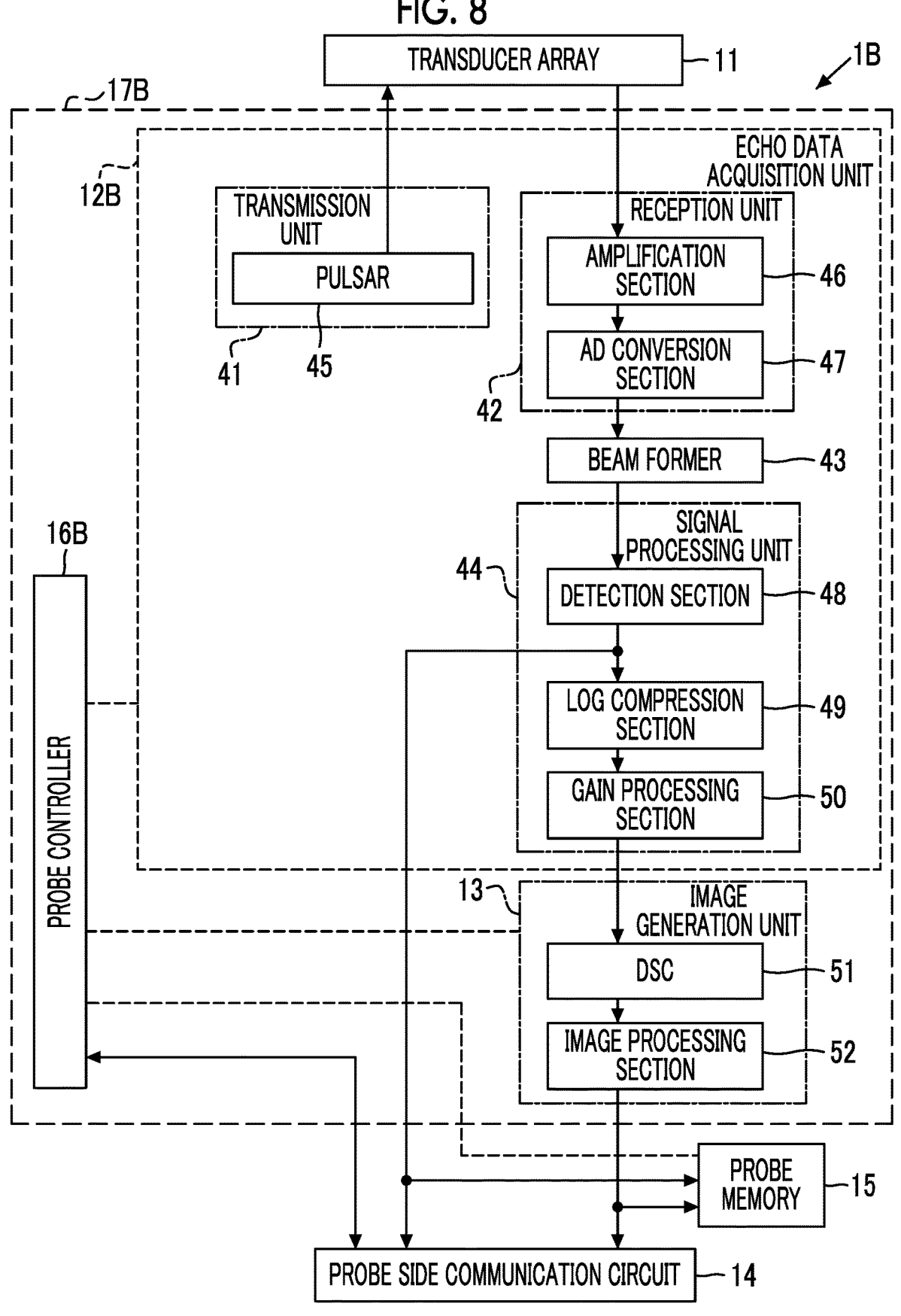
FIG. 8 is a block diagram showing an internal configu-
ration of an ultrasound probe of an ultrasound diagnostic
system according to Embodiment 3 of the present invention.

FIG. 8 shows an internal configuration of an ultrasound probe 1B of an ultrasound diagnostic system according to Embodiment 3 of the present invention. The ultrasound probe 1B uses an echo data acquisition unit 12B and a probe controller 16B instead of the echo data acquisition unit 12 and the probe controller 16 with respect to the ultrasound probe 1 in Embodiment 1 shown in FIG. 2, and other configurations are the same as those of the ultrasound probe 1 in Embodiment 1.

The echo data acquisition unit 12B has a configuration similar to the echo data acquisition unit 12 of the ultrasound probe 1 in Embodiment 1. However, in the ultrasound probe 1, the AD conversion section 47 of the reception unit 42 is connected to the probe side communication circuit 14, but in the ultrasound probe 1B in Embodiment 3, the detection section 48 of the signal processing unit 44 is connected to the probe side communication circuit 14.

The probe controller 16B is connected to the echo data acquisition unit 12B, the image generation unit 13, and the probe memory 15.

Further, a probe side processor 17B is composed of the echo data acquisition unit 12B, the image generation unit 13, and the probe controller 16B.

The detection section 48 of the signal processing unit 44 performs quadrature detection processing and filter processing on the sound ray signal sent out from the beam former 43 to convert the sound ray signal into a complex signal, but in the ultrasound probe 1B in Embodiment 3, the complex signal generated by the detection section 48 of the signal processing unit 44 is sent out to the probe memory 15 and the probe side communication circuit 14 as the echo data and is wirelessly transmitted to the diagnostic apparatus 3 under the control of the portable terminal 2.

The complex signal generated by the detection section 48 is also data including echo information that is before becoming the ultrasound image after gain processing. Therefore, even in the ultrasound diagnostic system according to Embodiment 3, by using the echo data wirelessly transmitted from the ultrasound probe 1B, the measurement unit 35 of the diagnostic apparatus 3 can execute advanced measurement, which cannot be achieved only by analyzing the ultrasound image.

In addition, in Embodiment 3, since the complex signal generated by the detection section 48 of the signal processing unit 44 is wirelessly transmitted to the diagnostic apparatus 3 as the echo data, it is also possible to generate so-called elastography which visualizes an elastic modulus, stiffness, and the like of the tissues inside the body of the subject.

Embodiment 4

Figure 9:
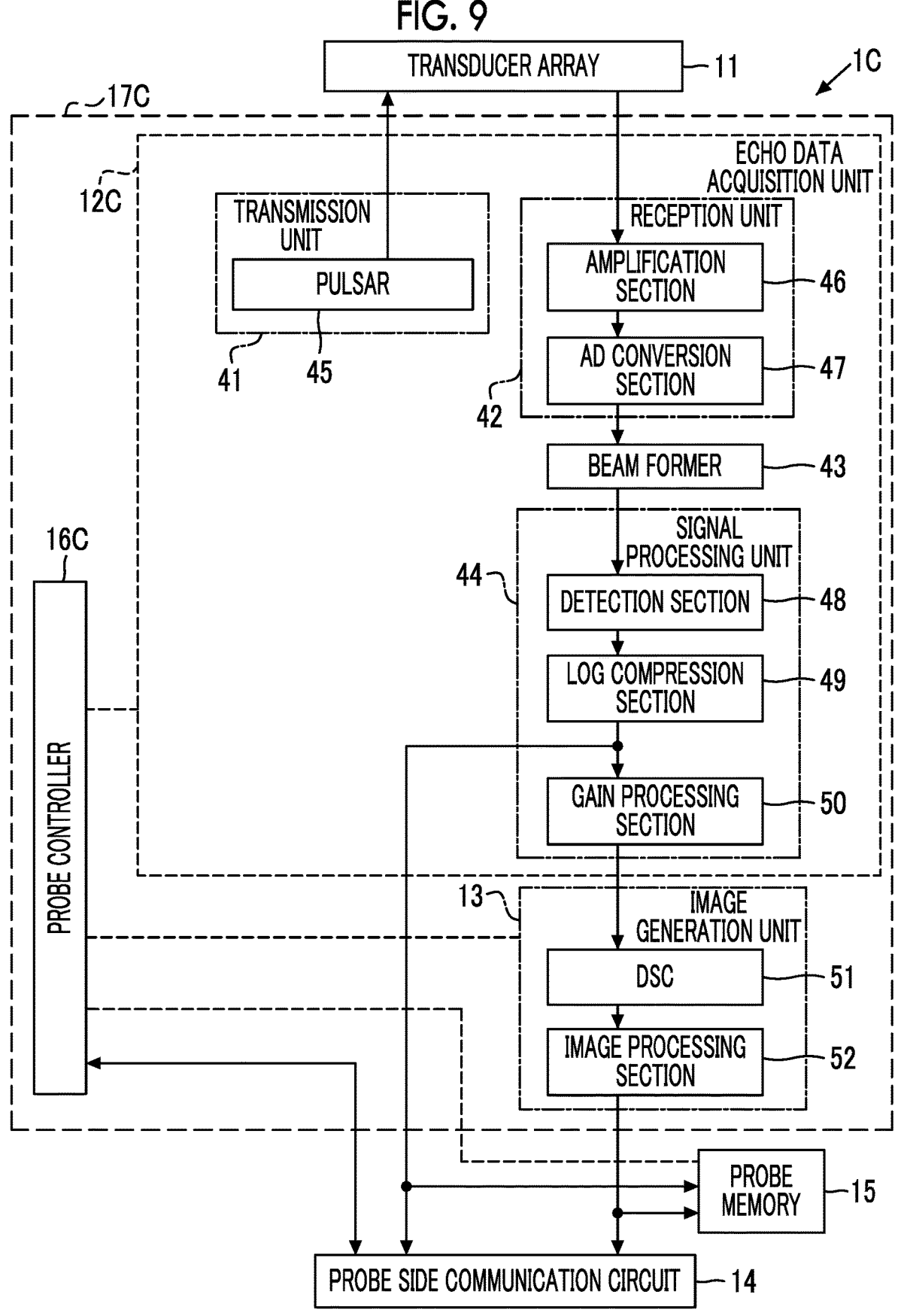
FIG. 9 is a block diagram showing an internal configu-
ration of an ultrasound probe of an ultrasound diagnostic
system according to Embodiment 4 of the present invention.

FIG. 9 shows an internal configuration of an ultrasound probe 1C of an ultrasound diagnostic system according to Embodiment 4 of the present invention. The ultrasound probe 1C uses an echo data acquisition unit 12C and a probe controller 16C instead of the echo data acquisition unit 12 and the probe controller 16 with respect to the ultrasound probe 1 in Embodiment 1 shown in FIG. 2, and other configurations are the same as those of the ultrasound probe 1 in Embodiment 1.

The echo data acquisition unit 12C has a configuration similar to the echo data acquisition unit 12 of the ultrasound probe 1 in Embodiment 1. However, in the ultrasound probe 1, the AD conversion section 47 of the reception unit 42 is connected to the probe side communication circuit 14, but in the ultrasound probe 1C in Embodiment 4, the log compression section 49 of the signal processing unit 44 is connected to the probe side communication circuit 14.

The probe controller 16C is connected to the echo data acquisition unit 12C, the image generation unit 13, and the probe memory 15.

Further, a probe side processor 17C is composed of the echo data acquisition unit 12C, the image generation unit 13, and the probe controller 16C.

The log compression section 49 of the signal processing unit 44 performs compression processing using logarithmic transformation on the complex signal converted by the detection section 48, but in the ultrasound probe 1C in Embodiment 4, the complex signal log-compressed by the log compression section 49 of the signal processing unit 44 is sent out to the probe memory 15 and the probe side communication circuit 14 as the echo data and is wirelessly transmitted to the diagnostic apparatus 3 under the control of the portable terminal 2.

The complex signal log-compressed by the log compression section 49 is also data including echo information that is before becoming the ultrasound image after gain processing. Therefore, even in the ultrasound diagnostic system according to Embodiment 4, by using the echo data wirelessly transmitted from the ultrasound probe 1C, the measurement unit 35 of the diagnostic apparatus 3 can execute advanced measurement, which cannot be achieved only by analyzing the ultrasound image.

Embodiment 5

Figure 10:
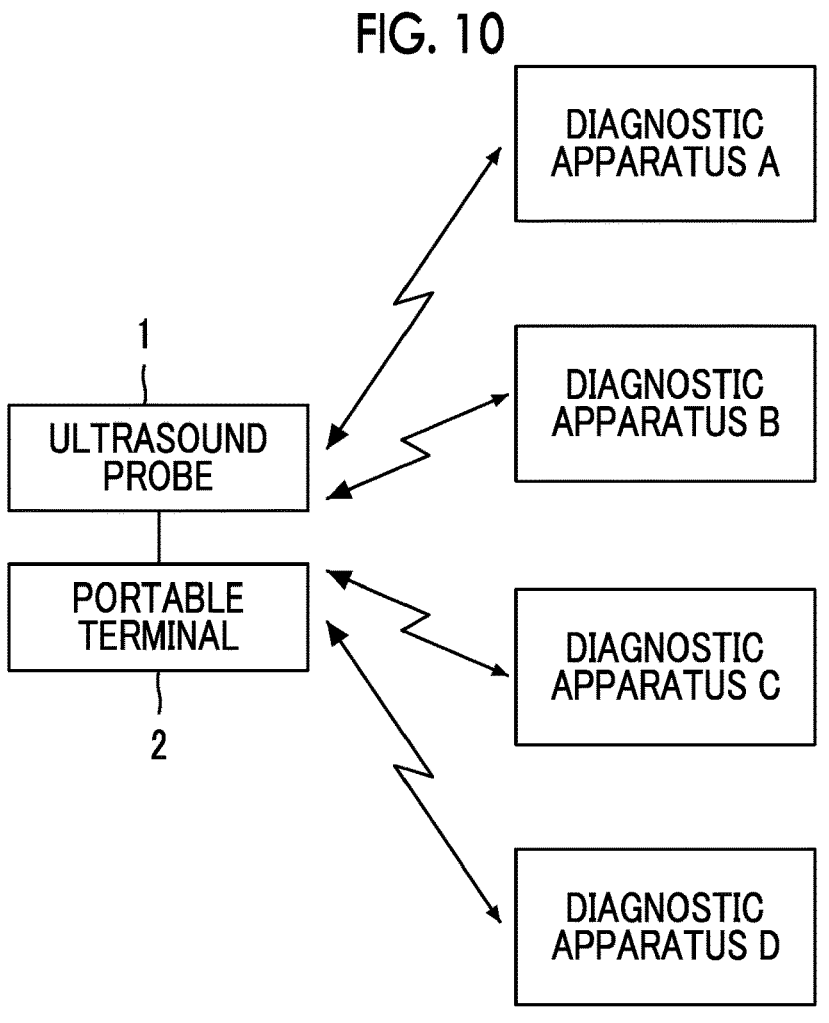
FIG. 10 is a block diagram showing a configuration of an
ultrasound diagnostic system according to Embodiment 5 of
the present invention.

FIG. 10 shows a configuration of an ultrasound diagnostic system according to Embodiment 5 of the present invention. A plurality of diagnostic apparatuses A to D are wirelessly connected to the ultrasound probe 1 and the portable terminal 2. The ultrasound probe 1 and the portable terminal 2 are wirelessly connected to each other, and the plurality of diagnostic apparatuses A to D are each wirelessly connected to both the ultrasound probe 1 and the portable terminal 2.

The plurality of diagnostic apparatuses A to D each have the same configuration as the diagnostic apparatus 3 shown in FIG. 1 and can execute a plurality of processing. However, due to differences in hardware specifications, the executable processing may not all be the same. That is, depending on the content of the processing, only some of the plurality of diagnostic apparatuses A to D may be able to execute the processing, and the remaining diagnostic apparatuses may not be able to execute the processing.

Figure 11:
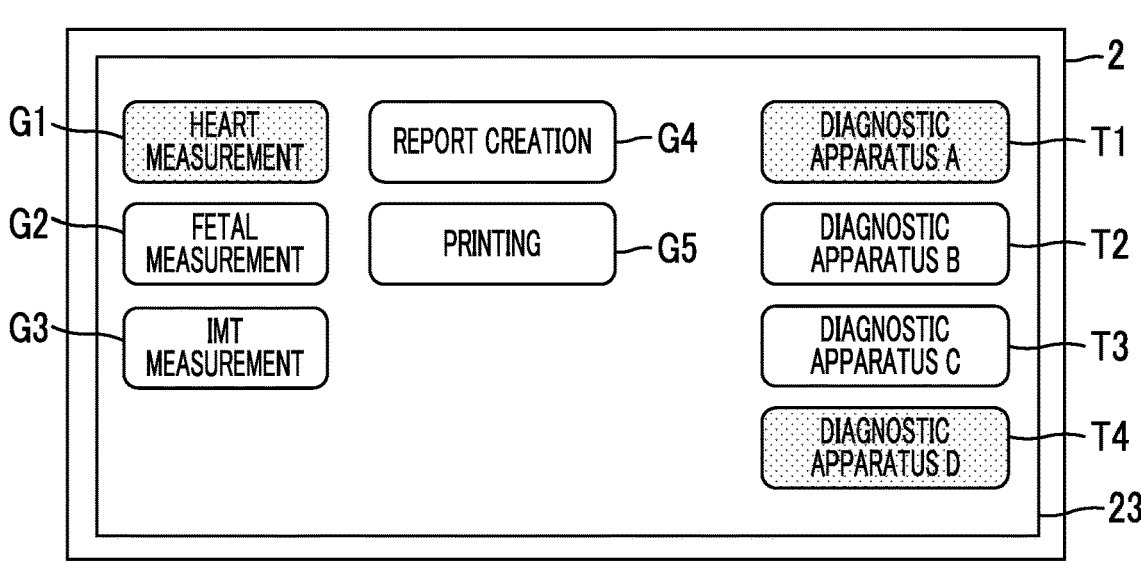
FIG. 11 is a diagram showing a display screen of a
terminal side monitor of a portable terminal in Embodiment
5 of the present invention.

As shown in FIG. 11, the portable terminal 2 can display the menu of the items G1 to G5 of the plurality of processing and apparatus selection buttons T1 to T4 representing the diagnostic apparatuses A to D on the terminal side monitor 23.

In addition, the portable terminal 2 wirelessly communicates with each of the diagnostic apparatuses A to D to check the activation state, the usage status, the examination function, and the like of each of the diagnostic apparatuses A to D, and in a case in which any of the items G1 to G5 is selected by the user from the menu displayed on the terminal side monitor 23 of the portable terminal 2, the apparatus selection buttons T1 to T4 corresponding to the diagnostic apparatus that can execute the processing of the selected item among the diagnostic apparatuses A to D are highlighted. The highlighting can be performed, for example, through highlighting of the apparatus selection button, color-coding, or the like.

For example, in the example shown in FIG. 11, the item G1 representing the heart measurement is selected by the user, and the apparatus selection button T1 of the diagnostic apparatus A and the apparatus selection button T4 of the diagnostic apparatus D, which can execute the heart measurement, are highlighted. Therefore, the user checks the terminal side monitor 23 to recognize that the heart measurement is executable by using the diagnostic apparatuses A and D among the diagnostic apparatuses A to D.

Then, for example, in a case in which the apparatus selection button T1 indicating the diagnostic apparatus A is selected by the user, the echo data is wirelessly transmitted from the ultrasound probe 1 to the diagnostic apparatus A under the control of the portable terminal 2, and the heart measurement is executed by the measurement unit 35 of the diagnostic apparatus A.

As described above, in the ultrasound diagnostic system according to Embodiment 5, the processing selected by the user can be executed by using the diagnostic apparatus that can execute the selected processing among the plurality of diagnostic apparatuses A to D, which makes it possible to perform more efficient ultrasound diagnosis.

The plurality of diagnostic apparatuses A to D are not limited to four, and two or more diagnostic apparatuses need only be wirelessly connected to the ultrasound probe 1 and the portable terminal 2.

In Embodiments 1 to 4 described above, the ultrasound probes 1, 1A, 1B, and 1C have the image generation unit 13, but the present invention is not limited to this, and the portable terminal 2 and the diagnostic apparatus 3 each have the image generation unit 13.

EXPLANATION OF REFERENCES 1, 1A, 1B, 1C: ultrasound probe
2: portable terminal
3: diagnostic apparatus
11: transducer array
12, 12A, 12B, 12C: echo data acquisition unit
13: image generation unit
14: probe side communication circuit
15: probe memory
16, 16A, 16B, 16C: probe controller
17, 17A, 17B, 17C: probe side processor
21: terminal side communication circuit
22, 32: display controller
23: terminal side monitor
24: terminal controller
25, 38: input device
26: terminal side processor
31: diagnostic apparatus side communication circuit
33: diagnostic apparatus side monitor
34: diagnostic apparatus memory
35: measurement unit
36: report creation unit
37: diagnostic apparatus controller 39: diagnostic apparatus side processor
41: transmission unit
42: reception unit
43: beam former
44: signal processing unit
45: pulsar
46: amplification section
47: AD conversion section
48: detection section
49: log compression section
50: gain processing section
51: DSC
52: image processing section
G1 to G5: item
U: ultrasound image
C1 to C13: command
T1 to T4: apparatus selection button

What is claimed is:

1. An ultrasound diagnostic system comprising:
an ultrasound probe;
a portable terminal; and
a diagnostic apparatus,
wherein the ultrasound probe, the portable terminal, and the diagnostic apparatus are wirelessly connected to each other,
the ultrasound probe has a memory and a probe-side processor that acquires echo data, including echo information before becoming an ultrasound image, through transmission and reception of an ultrasound wave with respect to a subject and stores the acquired echo data in the memory,
the portable terminal has a terminal-side processor that controls the ultrasound probe and the diagnostic apparatus such that the echo data stored in the memory is wirelessly transmitted from the ultrasound probe to the diagnostic apparatus,
the diagnostic apparatus has a diagnostic apparatus-side processor that performs measurements based on the echo data wirelessly transmitted from the ultrasound probe,
wherein the portable terminal has a terminal side monitor,
the terminal-side processor displays the ultrasound image generated based on the echo data on the terminal side monitor,
wherein the terminal-side processor displays, on the terminal side monitor, a plurality of processing items that are executable by the diagnostic apparatus, the plurality of processing items including at least one of a heart measurement, a fetal measurement, and an intima media thickness measurement,
a processing item selected by a user from among the plurality of processing items is transmitted from the portable terminal to the diagnostic apparatus, and
the diagnostic apparatus-side processor executes processing of the processing item transmitted from the portable terminal by using the echo data wirelessly transmitted from the ultrasound probe.

2. The ultrasound diagnostic system according to claim 1, wherein the ultrasound probe has a transducer array, and
the probe-side processor amplifies a reception signal output from the transducer array and converts the reception signal into a digital signal, phase-sums the digital signal thus converted, and generates an ultrasound image signal based on the signal thus phase-summed.

3. The ultrasound diagnostic system according to claim 2, wherein the probe-side processor wirelessly transmits the digital signal thus converted to the diagnostic apparatus as the echo data.

4. The ultrasound diagnostic system according to claim 3, wherein the terminal-side processor controls the ultrasound probe such that some pieces of the echo data designated by a user among the echo data stored in the memory are wirelessly transmitted to the diagnostic apparatus.

5. The ultrasound diagnostic system according to claim 3, wherein the portable terminal has a terminal side monitor, and
the terminal-side processor displays the ultrasound image generated based on the echo data on the terminal side monitor.

6. The ultrasound diagnostic system according to claim 2, wherein the probe-side processor wirelessly transmits the signal thus phase-summed to the diagnostic apparatus as the echo data.

7. The ultrasound diagnostic system according to claim 6, wherein the terminal-side processor controls the ultrasound probe such that some pieces of the echo data designated by a user among the echo data stored in the memory are wirelessly transmitted to the diagnostic apparatus.

8. The ultrasound diagnostic system according to claim 6, wherein the portable terminal has a terminal side monitor, and
the terminal-side processor displays the ultrasound image generated based on the echo data on the terminal side monitor.

9. The ultrasound diagnostic system according to claim 2, wherein the probe-side processor detects the signal thus phase-summed and generates a complex signal, log-compresses the complex signal thus generated, and performs gain processing on the signal thus log-compressed.

10. The ultrasound diagnostic system according to claim 9, wherein the probe-side processor wirelessly transmits the complex signal thus generated to the diagnostic apparatus as the echo data.

11. The ultrasound diagnostic system according to claim 10, wherein the terminal-side processor controls the ultrasound probe such that some pieces of the echo data designated by a user among the echo data stored in the memory are wirelessly transmitted to the diagnostic apparatus.

12. The ultrasound diagnostic system according to claim 10, wherein the portable terminal has a terminal side monitor, and
the terminal-side processor displays the ultrasound image generated based on the echo data on the terminal side monitor.

13. The ultrasound diagnostic system according to claim 9, wherein the probe-side processor wirelessly transmits the signal thus log-compressed to the diagnostic apparatus as the echo data.

14. The ultrasound diagnostic system according to claim 13, wherein the terminal-side processor controls the ultrasound probe such that some pieces of the echo data designated by a user among the echo data stored in the memory are wirelessly transmitted to the diagnostic apparatus.

15. The ultrasound diagnostic system according to claim 13, wherein the portable terminal has a terminal side monitor, and the terminal-side processor displays the ultrasound image generated based on the echo data on the terminal side monitor.

16. The ultrasound diagnostic system according to claim 1, wherein the terminal-side processor controls the ultrasound probe such that some pieces of the echo data designated by a user among the echo data stored in the memory are wirelessly transmitted to the diagnostic apparatus.

17. The ultrasound diagnostic system according to claim 1, wherein a plurality of the diagnostic apparatuses wirelessly connected to the ultrasound probe and the portable terminal are provided, the terminal-side processor displays, on the terminal side monitor, items of a plurality of processing that are executable by at least any of the plurality of diagnostic apparatuses, and in a case in which any of the items of the plurality of executable processing is selected by the user, the terminal-side processor displays, on the terminal side monitor, a diagnostic apparatus capable of executing processing of the item selected by the user among the plurality of diagnostic apparatuses.

18. The ultrasound diagnostic system according to claim 1, wherein the diagnostic apparatus-side processor is configured to perform creating a diagnostic report based on results of the measurements, and wherein the plurality of processing items includes a report creation.

19. A control method of an ultrasound diagnostic system including an ultrasound probe, a portable terminal, and a diagnostic apparatus wirelessly connected to each other, the control method comprising:

displaying on a terminal side monitor of the portable terminal a plurality of processing items that are executable by the diagnostic apparatus, the plurality of processing items including at least one of a heart measurement, a fetal measurement, and an intima media thickness measurement;

transmitting a processing item selected by a user from among the plurality of processing items from the portable terminal to the diagnostic apparatus;

acquiring echo data, including echo information before becoming an ultrasound image, through transmission and reception of an ultrasound wave with respect to a subject using the ultrasound probe;

storing the acquired echo data in a memory incorporated into the ultrasound probe;

controlling, through the portable terminal, the ultrasound probe and the diagnostic apparatus such that the echo data stored in the memory is wirelessly transmitted from the ultrasound probe to the diagnostic apparatus; and executing processing of the processing item transmitted from the portable terminal by the diagnostic apparatus based on the echo data wirelessly transmitted from the ultrasound probe.

\* \* \* \* \*